United States Patent
Kiya et al.

(10) Patent No.: US 10,995,689 B2
(45) Date of Patent: May 4, 2021

(54) EXHAUST GAS ANALYSIS METHOD AND EXHAUST GAS ANALYSIS SYSTEM

(71) Applicants: SUBARU CORPORATION, Tokyo (JP); HORIBA, LTD., Kyoto (JP)

(72) Inventors: Yasuyuki Kiya, Tokyo (JP); Shota Tobe, Tokyo (JP); Kunio Tabata, Kyoto (JP); Kenji Takeda, Kyoto (JP)

(73) Assignees: HORIBA, LTD., Kyoto (JP); SUBARU CORPORATION, Tokyo (JP)

( * ) Notice: Subject to any disclaimer, the term of this patent is extended or adjusted under 35 U.S.C. 154(b) by 0 days.

(21) Appl. No.: 16/418,356

(22) Filed: May 21, 2019

(65) Prior Publication Data
US 2019/0353106 A1    Nov. 21, 2019

(30) Foreign Application Priority Data
May 21, 2018  (JP) .............................. JP2018-097181

(51) Int. Cl.
| | |
|---|---|
| F02D 41/14 | (2006.01) |
| F02D 35/00 | (2006.01) |
| F02D 35/02 | (2006.01) |
| F02D 19/06 | (2006.01) |

(52) U.S. Cl.
CPC ..... *F02D 41/1466* (2013.01); *F02D 19/0639* (2013.01); *F02D 35/0015* (2013.01); *F02D 35/02* (2013.01); *F01N 2560/05* (2013.01); *Y02T 10/30* (2013.01)

(58) Field of Classification Search
None
See application file for complete search history.

(56) References Cited

U.S. PATENT DOCUMENTS

| | | | | |
|---|---|---|---|---|
| 4,990,780 A | * | 2/1991 | Lee .................. | G01N 21/39 250/339.13 |
| 5,445,964 A | * | 8/1995 | Lee .................. | G01N 21/39 250/343 |
| 7,905,137 B2 | * | 3/2011 | Taue ................ | F01M 11/10 73/114.56 |

(Continued)

FOREIGN PATENT DOCUMENTS

| | | | | |
|---|---|---|---|---|
| JP | 60-198433 A | | 10/1985 | |
| JP | 06093822 A | * | 4/1994 | ............ F01N 13/00 |

(Continued)

OTHER PUBLICATIONS

Hanaoka, Masanori, et al. "New Method for Measurement of Engine Oil Consumption (S-Trace Method)." SAE Transactions, vol. 88, 1979, pp. 3154-3161. JSTOR, www.jstor.org/stable/44648318. Accessed Apr. 15, 2020.*

(Continued)

*Primary Examiner* — Kevin R Steckbauer
(74) *Attorney, Agent, or Firm* — Brooks Kushman P.C.

(57) ABSTRACT

In order to separately evaluate an influence degree of fuel and an influence degree of lubricating oil with respect to particulate matters contained in exhaust gas, an exhaust gas analysis method includes: analyzing particulate matters contained in the exhaust gas exhausted from an engine, thereby making it possible to analyze the particulate matters derived from the lubricating oil by using isooctane as a fuel.

5 Claims, 4 Drawing Sheets

(56) References Cited

U.S. PATENT DOCUMENTS

| | | | | |
|---|---|---|---|---|
| 8,863,701 | B2* | 10/2014 | Imran | B01J 23/8986 |
| | | | | 123/3 |
| 9,267,429 | B2* | 2/2016 | Imran | F02B 43/12 |
| 2008/0250846 | A1* | 10/2008 | Taue | F01M 11/10 |
| | | | | 73/30.03 |
| 2013/0098314 | A1* | 4/2013 | Imran | B01J 35/0013 |
| | | | | 123/3 |
| 2014/0060008 | A1 | 3/2014 | Dittler et al. | |
| 2014/0216014 | A1 | 8/2014 | Hashida et al. | |
| 2015/0000615 | A1* | 1/2015 | Imran | F02B 43/12 |
| | | | | 123/3 |
| 2020/0340429 | A1* | 10/2020 | Cook | F02B 19/18 |

FOREIGN PATENT DOCUMENTS

| | | | |
|---|---|---|---|
| JP | 2011-241280 | A | 12/2011 |
| JP | 5994440 | B | 9/2016 |

OTHER PUBLICATIONS

Hanaoka, Masanori, et al. "New Method for Measurement of Engine Oil Consumption (S-Trace Method)." SAE Transactions, vol. 88, 1979, pp. 3154-3161. JSTOR, www.jstor.org/stable/44648318. Accessed Apr. 15, 2020. (Year: 1979).*

EESR dated Oct. 21, 2019 issued for European Patent Application No. 19 175 747.5, 11 pgs.

Trinker F H et al., "The Effect of Fuel-oil Solubility on Exhaust HC Emissions", SAE Technical Paper Series, Society of Automotive Engineers, Warrendale, PA, US, No. 912349, Oct. 1, 1991, pp. 1-11, XP009516568, ISSN: 0148-7191, DOI: 10.4271/912349.

Edward W Kaiser et al., "Effect of Fuel Structure on Emissions From a Spark-Ignited Engine", Environ. Sci. Technol., vol. 25, No. 12, Dec. 1, 1991, pp. 2005-2012, XP055630722.

W. O. Siegl et al., "Speciated Hydrocarbon Emissions From the Combustion of Single Component Fuels. I. Effect of Fuel Structure", Journal of the Air and Waste Management Association, vol. 42, No. 7, Jul. 1, 1992, pp. 912-920, XP055630647, US, ISSN: 1047-3289, DOI: 10.1080/10473289,1992. 10467041.

* cited by examiner

EXHAUST GAS ANALYSIS METHOD AND EXHAUST GAS ANALYSIS SYSTEM

CROSS-REFERENCE TO RELATED APPLICATIONS

This application claims priority to Japanese Patent Application No. 2018-097181, filed on May 21, 2018, the disclosure of which is incorporated by reference herein.

TECHNICAL FIELD

The present disclosure relates to an exhaust gas analysis method and exhaust gas analysis system for analyzing at least particulate matter derived from lubricating oil among particulate matters contained in exhaust gas from an engine.

BACKGROUND ART

In recent years, there is concern about an influence of particulate matters contained in exhaust gas from an engine on human bodies, and Patent Literature 1 discloses a method for producing a fuel with a reduced exhaust amount of particulate matters. In this method, there is disclosed an index called PM Index which is calculated using a calculation formula (1) as following:

$$PM\ \text{Index} = \sum_{i=1}^{n} \frac{DBE_i + 1}{V.P(443\ K)_i} \times Wt_i \qquad (1)$$

In the calculation formula (1), i is a number corresponding to each of n pieces of components contained in the fuel, $V.P(443K)_i$ is a vapor pressure at an absolute temperature of 443K of the i-th component, $DBE_i$ is a double bond equivalent of the i-th component, and $Wt_i$ is a weight percent of the i-th component contained in the fuel.

Under such circumstances, in order to further reduce the particulate matters contained in the exhaust gas, it is necessary to analyze generation factors of the particulate matters in detail under various driving conditions. For example, in the case where exhaust gas from an engine of a gasoline car is analyzed, it is considered that the particulate matters derived from the fuel and the particulate matters derived from lubricating oil are contained in the exhaust gas.

However, there has been no method for quantitatively separating an influence degree of fuel on the particulate matters contained in the exhaust gas and an influence degree of the lubricating oil on the particulate matters contained in the exhaust gas. Therefore, it has been difficult to perform measurement of the ratio of the particulate matters derived from the fuel and the particulate matters derived from the lubricating oil, quantification of the respective particulate matters, and the like.

CITATION LIST

Patent Literatures

Patent Literature 1: Japanese Unexamined Patent Application Publication No. 2011-241280

SUMMARY

Technical Problem

Therefore, the present invention has been made in order to solve the above-described problems, and a main object thereof is to make it possible to separately evaluate an influence degree of fuel and an influence degree of lubricating oil with respect to particulate matters contained in exhaust gas.

Solution to Problem

That is, an exhaust gas analysis method according to an embodiment of the present invention is intended to analyze exhaust gas exhausted from an engine, and in the case where isooctane is used as a fuel for the engine, the exhaust gas exhausted from the engine is analyzed and particulate matters contained in the analyzed exhaust gas is measured as particulate matters derived from lubricating oil.

According to such an exhaust gas analysis method, by using isooctane as the fuel, the particulate matters contained in the exhaust gas exhausted from the engine is analyzed as the particulate matters derived from the lubricating oil, and therefore the particulate matters derived from the lubricating oil can be analyzed separately from the particulate matters derived from the fuel, and an influence degree of the lubricating oil on the particulate matters contained in the exhaust gas can be evaluated separately from an influence degree of the fuel on the particulate matters contained in the exhaust gas.

In order to compare the numbers and/or masses of particulate matters under various operating conditions, it is preferable that, upon changing the operating conditions of the engine, the number and/or mass of the particulate matters contained in the exhaust gas exhausted from the engine is measured.

As the operating conditions described above, there can be listed a revolution speed of the engine, a load applied to the engine, a temperature of coolant of the engine, and the like.

Further, it is preferable that, a total sulfur component concentration contained in the exhaust gas is measured as a concentration of the sulfur component derived from the lubricating oil, and a consumption amount of the lubricating oil is calculated based on the total sulfur component concentration, and then the consumption amount is associated with the measurement result of the particulate matters derived from the lubricating oil.

In this way, it is possible to know, for example, a correlation between the consumption amount of the lubricating oil and a generation amount of the particulate matters derived from the lubricating oil.

Further, an exhaust gas analysis system according to an embodiment of the present invention is intended to analyze exhaust gas exhausted from an engine, including: an exhaust gas collecting unit adapted to collect the exhaust gas exhausted from the engine in the case where isooctane is used as a fuel for the engine; and an exhaust gas analyzer adapted to analyze the exhaust gas collected by the exhaust gas collecting unit and measure particulate matters contained in the analyzed exhaust gas as particulate matters derived from lubricating oil.

With this exhaust gas analysis system, it is possible to have an effect similar to that of the exhaust gas analysis method mentioned above.

Advantageous Effects

According to the embodiment of the present invention configured as described above, it is possible to separately evaluate the influence degree of the fuel on the particulate matters contained in the exhaust gas and the influence degree of the lubricating oil on the particulate matters contained in the exhaust gas, thereby contributing to further reduction of the particulate matters contained in the exhaust gas.

DESCRIPTION OF EMBODIMENTS

In the following, one embodiment of the present invention will be described with reference to the drawings.

First, an exhaust gas analysis system for use in the present embodiment will be described.

Figure 1:
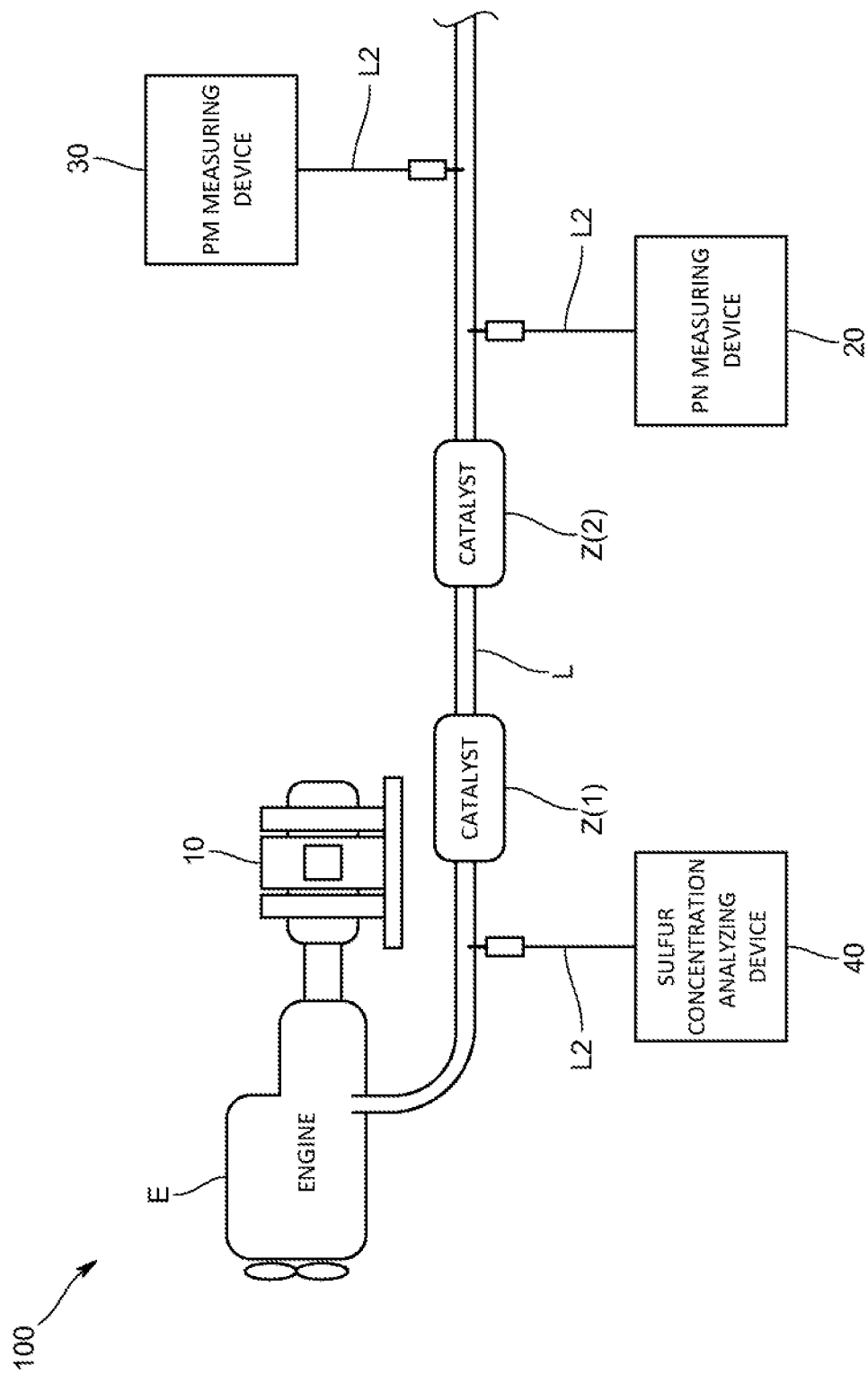
FIG. 1 is a schematic diagram showing an overall configuration of an exhaust gas analysis system according to the present embodiment.

The exhaust gas analysis system 100 is used to analyze particulate matters contained in exhaust gas exhausted from an engine E. As shown in FIG. 1, the exhaust gas analysis system 100 includes: a dynamometer 10 for applying a load to the engine E; an exhaust gas flow path L connected to the engine E; a PN measuring device 20 for measuring the number of particulate matters (referred to as "PN" hereinafter) contained in the exhaust gas, a PM measuring device 30 for measuring a mass of the particulate matters (referred to as "PM" hereinafter) contained in the exhaust gas; and an exhaust gas collecting unit L2 (also, referred to as "exhaust gas collecting flow path L2" hereinafter) for introducing the exhaust gas from the exhaust gas flow path L to each of the PN measuring device 20 and the PM measuring device 30. The exhaust gas analysis system 100 may be configured to connect an engine dynamo to the engine E alone, it may be configured to connect the dynamo to a drive system on which the engine E is mounted, and it may be also configured to mount a vehicle on a chassis dynamo.

The exhaust gas flow path L has its upstream side connected to an exhaust port (not shown) of the engine E, and the exhaust gas flow path L is provided with catalysts Z (here, an upstream side catalyst Z1 and a downstream side catalyst Z2) for purifying the exhaust gas.

The exhaust gas is sampled from the exhaust gas flow path L and introduced into the PN measuring device 20 through the exhaust gas collecting flow path L2 (i.e., the exhaust gas collecting unit L2). The PN measuring device 20 is configure to count the PN by using a detector such as a laser scattering condensed particle counter (CPC). Specifically, as the PN measuring device 20, there is used an exhaust gas analyzer called MEXA-2100 SPCS manufactured by Horiba, Ltd., and it is configured to adhere organic gas such as alcohol or butanol to the particulate matters contained in the exhaust gas, thereby making the particulate matters to be grown to have large diameters, and then the particulate matters are irradiated with laser light for counting the number thereof.

Similarly, the exhaust gas sampled from the exhaust gas flow path L is introduced into the PM measuring device 30 through the exhaust gas collecting flow path L2 (i.e., the exhaust gas collecting unit L2). The PM measuring device 30 is configured to measure the particulate matters collected by a filter (not shown). That is, the PM measuring device 30 is configured to measure the total mass of the particulate matters contained in the sampled exhaust gas, and there is used an exhaust gas analyzer called MEXA-1370PM manufactured by Horiba, Ltd., as the PM measuring device 30. Specifically, for example, the PM measuring device 30 is configured to vaporize and thermally decompose the collected particulate matters, gasify the same by an oxidation-reduction reaction, and then measure the total mass of soluble organic components (SOF), soot and sulfate components contained in the sampled exhaust gas as the particulate matters.

As shown in FIG. 1, the exhaust gas analysis system 100 of the present embodiment further includes a sulfur concentration analyzer 40 that analyzes concentration of sulfur components contained in the exhaust gas.

Similarly, the exhaust gas sampled from the exhaust gas flow path L is introduced into the sulfur concentration analyzer 40 through the exhaust gas collecting flow path L2 such as a heating pipe and the like. The sulfur concentration analyzer 40 is configured to measure the sulfur concentration contained in the sampled exhaust gas. As the sulfur concentration analyzer 40, there is used an exhaust gas analyzer called MEXA-1170SX manufactured by Horiba, Ltd. Here, a sampling point is positioned, for example, on the upstream side of the catalysts Z (here, the upstream side catalyst Z1) in the exhaust gas flow path L. Specifically, the sulfur concentration analyzer 40 is configured to measure the total sulfur components contained in the sampled exhaust gas. Further, in addition to total reducing sulfur such as hydrogen sulfide ($H_2S$) which is a gas component and methanethiol ($CH_3SH$), sulfate as the particulate matters contained in the sampled exhaust gas is converted to sulfur dioxide ($SO_2$), and the concentration of these sulfur components is measured using, for example, an Ultra Violet Fluorescence (UVF) method.

Next, an embodiment of an exhaust gas analysis method according to the present invention will be described. This method is directed to analysis of particulate matters contained in the exhaust gas exhausted from the engine E, using the exhaust gas analysis system 100 described above. The embodiment of an exhaust gas analysis method has been made based on the fact that the inventor of the present invention has earnestly examined a method for separating the influence degree of the fuel and that of the lubrication oil affecting on the particulate matters. Specifically, the inventor of the present disclosure found that, by using isooctane having an octane number of 100 as the fuel, the particulate matters are hardly derived from the fuel but the particulate matters contained in the exhaust gas are substantially derived from the lubricating oil.

In view of the above knowledge, the embodiment of the exhaust gas analysis method according to the embodiment of the present invention has a specific feature that, by using isooctane as the fuel for the engine E, the particulate matters contained in the exhaust gas are analyzed, regarding as the particulate matters substantially derived from the lubricating oil.

As an example of the engine E, there may be used a direct injection gasoline engine which is a kind of a gasoline engine, and as an example of the lubricating oil, there may be used commercially available 0W-20 oil (API: equivalent to SN standard, sulfur concentration 2.695 ppm). The engine E may be a port injection engine.

Figure 2:
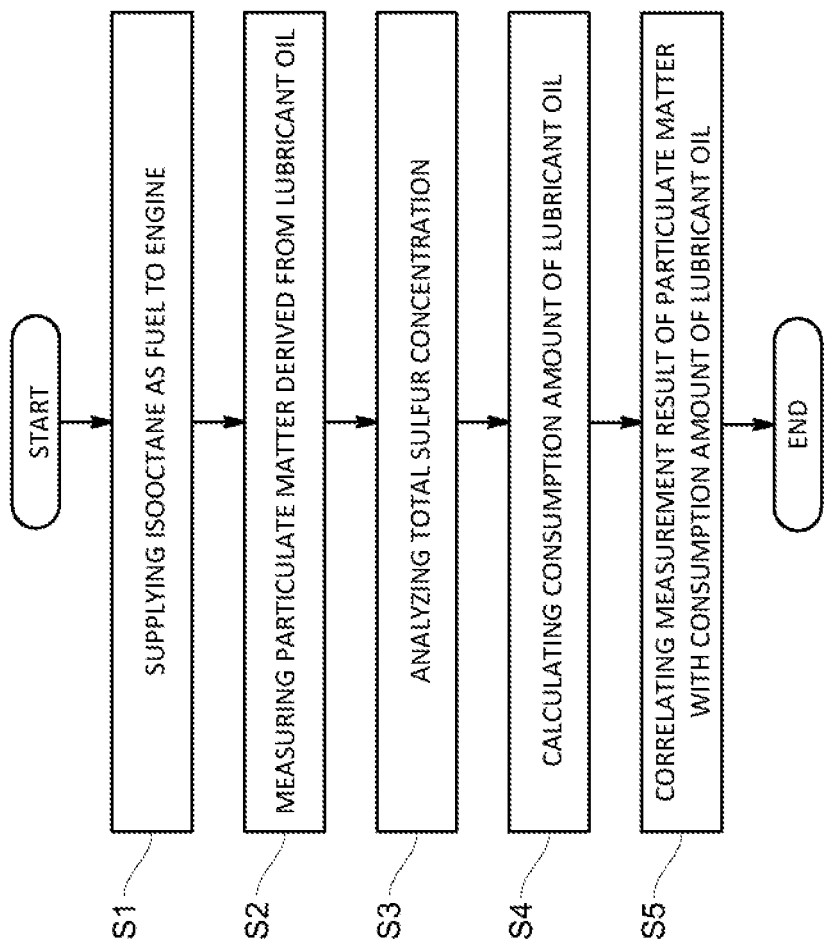
FIG. 2 is a flowchart showing an exhaust gas analysis method of the embodiment.

Hereinafter, the embodiment of the analysis method of the present invention will be described in detail with reference to the flowchart shown in FIG. 2.

First, isooctane as the fuel is supplied to the engine E (S1). Isooctane is 2,2,4-trimethylpentane ($C_8H_{18}$) and this fuel has an octane number of 100, as shown in Table 1. Further, it is understood that the isooctane fuel has a very low PM Index, which is used as an index of an exhaust number of aroma components and particulate matters, as compared to, for example, gasoline of general properties distributed in Japan. In Table 1, PM Index is a value calculated using the calculation Formula (1) described in the background art.

TABLE 1

| Item | Isooctane | Gasoline |
|---|---|---|
| Octane number | 100 | 95 |
| Sulfur concentration [ppm] | 0 | 6 |
| Aroma component [vol %] | 0.2 | 30.2 |
| PM Index | 0.2 | 1.2 |

Then, the engine E is started to analyze the particulate matters contained in the exhaust gas. Here, as described above, since the isooctane fuel has an octane number of 100 and has very low aroma components and PM index, substantially no particulate matters derived from the fuel is generated. Hence, the particulate matters contained in the exhaust gas can be regarded as those derived from the lubricating oil.

Therefore, the particulate matters contained in the exhaust gas are measured, regarding as the particulate matters derived from the lubricating oil (S2). Specifically, the PN contained in the exhaust gas is measured regarding as those derived from the lubricating oil, using the PN measuring device 20 described above, and the PM contained in the exhaust gas is measured regarding as those derived from the lubricating oil, using the PM measuring device 30 described above.

Furthermore, in the present embodiment, the total sulfur concentration (TS) contained in the exhaust gas is analyzed, using the sulfur concentration analyzer 40 described above (S3).

Here, since the isooctane fuel does not contain a sulfur component, the total sulfur concentration (TS) analyzed in Step S3 can be regarded as the concentration of the sulfur component derived from the lubricating oil. By using a so-called S tracing method, a consumption amount of the lubricating oil is calculated based on the total sulfur concentration (TS) obtained in Step S3 (S4). Specifically, the consumption amount of the lubricating oil can be calculated according to a predetermined calculation formula in which the total sulfur concentration (TS), the concentration of sulfur components in the lubricating oil or the like are used as parameters.

Thus, by measuring the PN and the PM derived from the lubricating oil in Step S2 and calculating the consumption amount of the lubricating oil in Step S4, the measurement results of the particulate matters derived from the lubricating oil can be correlated. That is, it is possible to correlate the PN and the PM derived from the lubricating oil with the consumption amount of the lubricating oil (S5).

Thus, according to the embodiment of the exhaust gas analysis method described above, by using isooctane as the fuel, the particulate matters contained in the exhaust gas exhausted from the engine E can be analyzed regarding as the particulate matters derived from the lubricating oil. Hence, the particulate matters derived from the lubricant oil can be analyzed separately from the particulate matters derived from the fuel.

So, experimental results which evaluated the influence degree of the lubricating oil separately from the influence degree of the fuel with respect to the particulate matters contained in the exhaust gas will be described below using this exhaust gas analysis method.

<PN Measurement>

Figure 3:
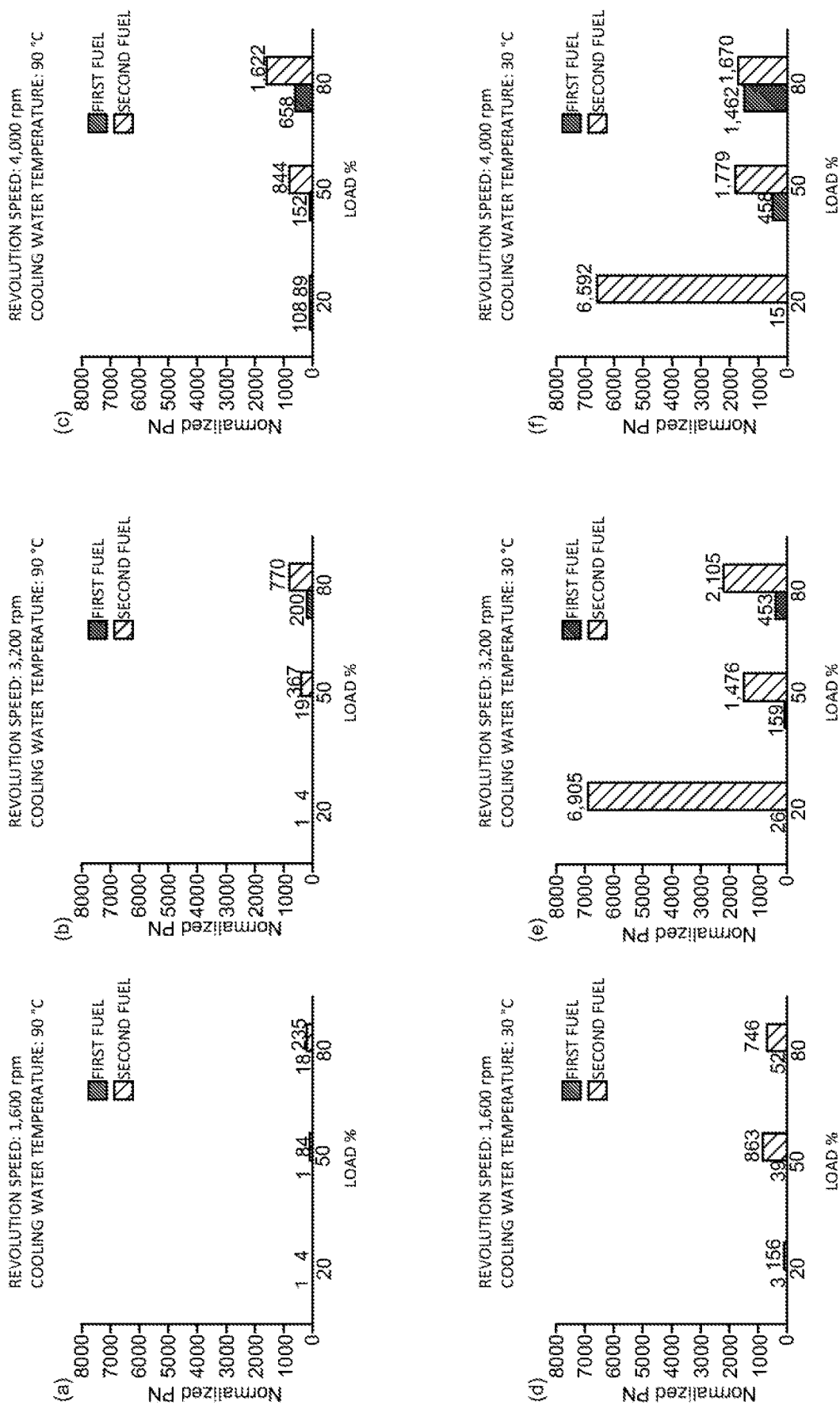
FIG. 3 shows measurement results of PN under conditions of cooling water temperatures of 90° C. and 30° C.

The PN derived from the fuel is affected by combustion conditions such as an injection method and injection timing of the fuel, a temperature of a fuel chamber and an air-fuel ratio. Therefore, in each of the cases of using isooctane as the first fuel and using gasoline of a general property as the second fuel, operating conditions of the engine E, for example, a revolution speed of the engine E, a load given to the engine E from the dynamometer 10, a cooling water temperature of the engine E, and the like are variously changed. FIG. 3 shows the results of measuring the PN before and after changing the operating conditions. A preferred method of measuring the PN will be described with reference to FIG. 3.

First, the results of measuring the PN exhaust amount at a cooling water temperature of 90° C. are shown in FIGS. 3 (a) to 3 (c).

Under these conditions, it can be found that the PN exhaust amounts tend to increase as the load to the engine increases and the revolution speed increases in the case of using either the first fuel or the second fuel. Further, it is found that the PN exhaust amount is larger in the case of using the second fuel compared to the case of using the first fuel, and that an increasing rate of the PN exhaust amount is increasing in a high load side and a high revolution speed side in the case of using the second fuel, with regard to that in the case of using the first fuel as a reference.

Regarding the measurement results with respect to the various revolution speeds, it is presumed that, the reason why the resultant PN exhaust amount increases as the increase of the revolution speed increases in the case of using the first fuel is because the amount of the oil flowing into the combustion chamber via a piston sliding portion and a blow-by gas reduction circuit increases due to scraping of the oil caused by a crank rotation movement.

Moreover, regarding the comparison of the PN exhaust amounts between the cases of using the first fuel and the second fuel, it is presumed that, the reason why the resultant PN exhaust amount is larger in the case of using the second fuel compared to the case of using the first fuel is because a difference in PM Indexes between the first fuel and the second fuel, i.e., a difference in risks of generating the particulate matters is affected.

Furthermore, it is presumed that, the reason why the resultant increasing rate of the PN exhaust amount is smaller in a low load side in the case of using the second fuel with regard to that in the case of using the first fuel as a reference is because the fuel influence degree on the total PN exhaust amount is also small in a low load operating region where a fuel injection amount is relatively small.

Next, the results of measuring the PN exhaust amount at a cooling water temperature of 30° C. are shown in FIGS. 3 (d) to 3(f).

Under this condition, it was observed that the PN exhaust amounts increased in the case of using either the first fuel or the second fuel, as compared to the condition of the cooling water temperature of 90° C. Further, unlike the condition of the cooling water temperature of 90° C., no correlation was found between the PN exhaust amount of the second fuel and the load to the engine and the revolution speed of the engine.

<Measurement Result of Quantitatively Separating Particulate Matters Derived from Fuel and Particulate Matters Derived from Lubricating Oil>

Figure 4:
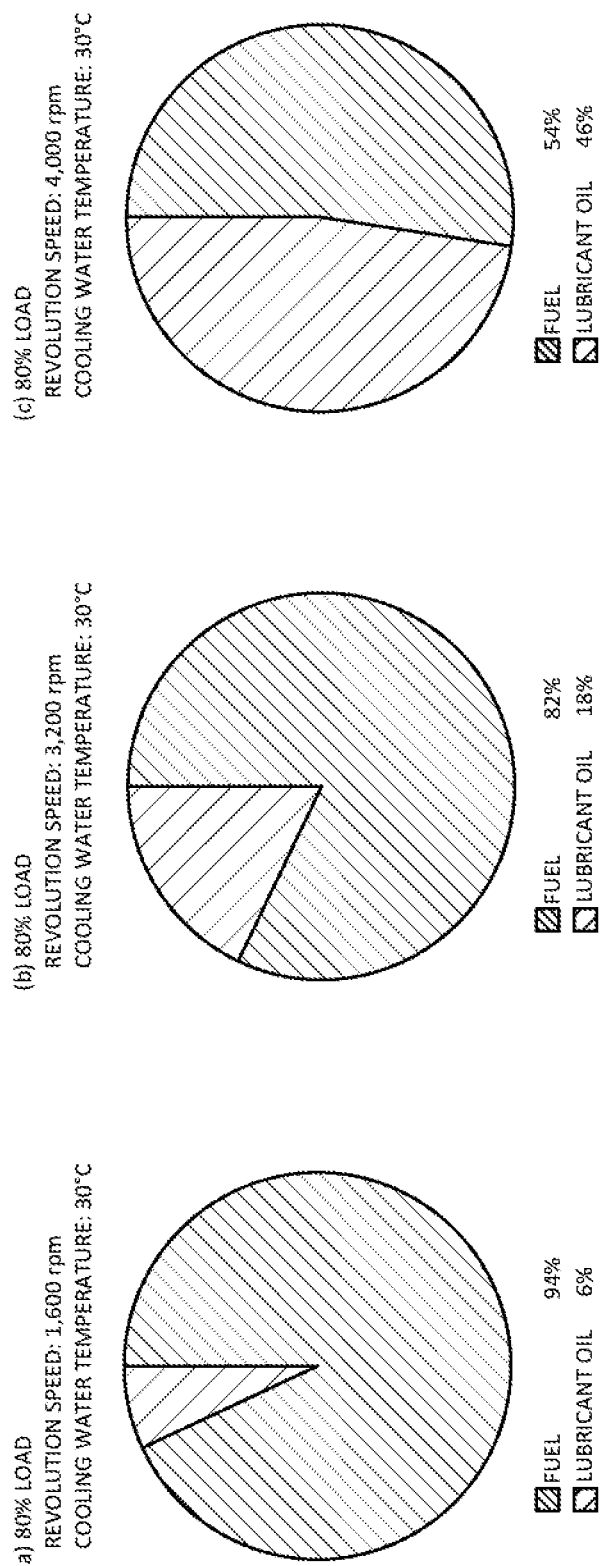
FIG. 4 shows measurement results of PN in each case where an engine was operated under various operating conditions.

Subsequently, the results of evaluating the particulate matters derived from the fuel (i.e., gasoline of general properties) while separating the same from the particulate matters derived from the lubricating oil are shown in FIGS. 4 (a) to 4 (c).

The evaluation results shown in FIGS. 4 (a) to 4 (c) are the results in the case where the revolution speed is changed while keeping the cooling water temperature and the load constant, and these are shown as pie charts of the measurement results in the case of the load being 80% in FIGS. 3 (d) to 3 (f). As can be seen from the results, it is understood that the influence of the lubricating oil also increases as the revolution speed increases. As described above, this is considered that a movement of the amount of the oil flowing into the combustion chamber being increased as the revolution speed being increased is captured.

As described above, according to the exhaust gas analysis method according to the present embodiment, by isooctane as the fuel, the particulate matters contained in the exhaust gas exhausted from the engine can be analyzed regarding as the particulate matters derived from the lubricating oil. Thus, the particulate matters derived from the lubricating oil can be analyzed while separately the same from the particulate matters derived from the fuel. Accordingly, it becomes possible to evaluate quantitatively the influence degree of the lubricating oil on the particulate matters contained in the exhaust gas while separately the same from the influence degree of the fuel.

Further, in the case where isooctane is used as the fuel, since a sulfur component is not contained in isooctane, the total sulfur component concentration contained in the exhaust gas to be analyzed by the sulfur concentration analyzer 40 can be regarded as the concentration of the sulfur component derived from the lubricating oil. Thus, it is possible to calculate the consumption amount of the lubricating oil by S-trace method based on the analyzed total sulfur component concentration, and therefore, it is possible to correlate the PN and the PM derived from the lubricating oil with the consumption amount of the lubricating oil.

Note that, the embodiment of the present invention is not limited to the above embodiments.

For example, in the above embodiments, both the PN and the PM are measured, but only either the PN or the PM may be measured.

In the above embodiments, although the PN and the PM are measured while changing the revolution speed of the engine E, the load applied to the engine E from the dynamometer 10, or the temperature of the cooling water regarding as the operating conditions of the engine E, the PN and the PM may be measured by changing the combustion conditions such as a fuel ratio and an injection timing of the fuel, and the like.

Furthermore, it may be also possible to subtract the analysis result of the particulate matters in the case where isooctane is used as the first fuel from the analysis result of the particulate matters in the case where, for example, gasoline having a general property is used as the second fuel.

In this way, by using isooctane as the first fuel, the particulate matters derived from the lubricating oil can be analyzed as described in the above embodiment. Therefore, by subtracting the analysis result thereof from the analysis result obtained by using gasoline as the second fuel, the particulate matters derived from gasoline can be analyzed while separated the same from the particulate matters derived from the lubricating oil. As a result, it is possible to evaluate the degree of influence of gasoline on the particulate matters contained in the exhaust gas while separately the same from the influence degree of the lubricating oil.

In addition, various modifications and combinations of the embodiments may be made without departing from the spirit of the present invention.

REFERENCE SIGNS LIST

100: Exhaust gas analysis system
E: Engine
10: Dynamometer
L: Exhaust gas flow path
L2: Exhaust gas collection part
20: PN measuring device
30: PM measuring device
40: Sulfur concentration analyzer

The invention claimed is:

1. An exhaust gas analysis method for analyzing exhaust gas exhausted from an engine comprising:
   supplying only isooctane to the engine as a fuel;
   analyzing exhaust gas exhausted from the engine while supplying only isooctane to the engine as a fuel; and
   measuring particulate matters contained in the analyzed exhaust gas as particulate matters derived only from lubrication oil in the engine.

2. The exhaust gas analysis method according to claim 1, wherein, responsive to changing operating conditions of the engine, a number or mass of the particulate matters contained in the exhaust gas exhausted from the engine is measured.

3. The exhaust gas analysis method according to claim 2, wherein at least one of a revolution speed of the engine, a load applied to the engine, and a temperature of coolant of the engine is included as the operating conditions.

4. The exhaust gas analysis method according to claim 1, further comprising:
   measuring a total sulfur component concentration contained in the exhaust gas as a concentration of a sulfur component derived from the lubricating oil;
   calculating a consumption amount of the lubricating oil based on the total sulfur component concentration; and
   linking the consumption amount with the measurement result of the particulate matters derived from the lubricating oil.

5. The exhaust gas analysis method according to claim 1, wherein the engine is a gasoline engine.

* * * * *